United States Patent [19]

Haas et al.

[11] Patent Number: 4,493,909
[45] Date of Patent: Jan. 15, 1985

[54] POLY-N,N-HYDROXYALKYLAMIDES OF POLYBASIC CARBOXYLIC ACIDS AND A PROCESS FOR THE PRODUCTION THEREOF

[75] Inventors: Peter Haas, Haan; Hans Hettel, Cologne, both of Fed. Rep. of Germany

[73] Assignee: Bayer Aktiengesellschaft, Leverkusen, Fed. Rep. of Germany

[21] Appl. No.: 386,129

[22] Filed: Jun. 7, 1982

[30] Foreign Application Priority Data

Jun. 25, 1981 [DE] Fed. Rep. of Germany ....... 3124885
Dec. 18, 1981 [DE] Fed. Rep. of Germany ....... 3150269

[51] Int. Cl.³ .................. C08G 18/14; C08G 18/18; C08G 18/20
[52] U.S. Cl. ................... 521/166; 521/118; 528/58
[58] Field of Search ............ 521/166, 118; 528/58

[56] References Cited

U.S. PATENT DOCUMENTS

| 3,748,288 | 7/1973 | Winkler et al. | 521/52 |
| 3,884,848 | 5/1975 | Ricciardi et al. | 521/130 |
| 3,981,828 | 9/1976 | Demou et al. | 521/110 |
| 4,076,917 | 2/1978 | Swift et al. | 526/49 |

FOREIGN PATENT DOCUMENTS

| 294429 | 9/1965 | Austria . |
| 028469 | 5/1981 | European Pat. Off. . |
| 1032873 | 6/1966 | United Kingdom . |
| 1143724 | 2/1969 | United Kingdom . |
| 1384771 | 2/1975 | United Kingdom . |
| 2010265 | 6/1979 | United Kingdom . |
| 2025439 | 1/1980 | United Kingdom . |

OTHER PUBLICATIONS

Chemical Abstracts Band 95, No. 8, Aug. 24, 1981, Yangol et al, "Poly(ethyl-amide-urethane) Coatings", p. 81, Abstract No. 63778s.
Chemical Abstracts Band 81, No. 7, Aug. 19, 1974, Kobayashi et al., "Amido Acrylates", Abstract No. 37268s.

*Primary Examiner*—John Kight
*Assistant Examiner*—Marvin L. Moore
*Attorney, Agent, or Firm*—Gene Harsh; Joseph C. Gil; Lyndanne M. Whalen

[57] ABSTRACT

A polycarboxylic acid alkyl or aryl ester corresponding to the formula

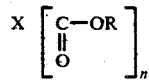

is reacted with a dialkanolamine corresponding to the formula $$HN(A-OH)_2$$

at a temperature from 50° to 200° C. The alcohol ROH formed during this reaction is removed from the reaction mixture and the product recovered corresponds to the formula

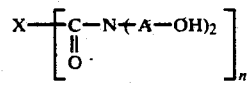

in which the radicals n, X, A and R are as defined herein. The thus-produced poly-N,N-hydroxyalkylamides are particularly useful as cell-opening materials in the production of elastic polyurethane foams.

16 Claims, No Drawings

POLY-N,N-HYDROXYALKYLAMIDES OF POLYBASIC CARBOXYLIC ACIDS AND A PROCESS FOR THE PRODUCTION THEREOF

BACKGROUND OF THE INVENTION

This invention relates to poly-N,N-hydroxyalkylamides of polybasic carboxylic acids and to a process for their production. These polyamides are particularly useful as cell-opening components in the production of highly elastic polyurethane foams.

Experience in the commercial production of highly elastic polyurethane foams has shown that, despite a high level of technical development, production still involves risks in regard to foam quality. More specifically, such foams are prone to shrinkage which results in an uneven distribution of mechanical properties over the cross-section of the foam block. The entire surface of the foam may be so seriously affected by this compression phenomenon that the product foam is rendered virtually useless.

In the production of cold foams, it has been standard practice to counteract some of the shrinkage and cell size problems by addition of stabilizers. (See for example U.S. Pat. No. 3,748,288 and German Offenlegungsschrift Nos. 22 10 721 and 24 54 049), although this causes deterioration of the mechanical properties of the foams, particularly in their compression hardness. Thus, although German Offenlegungsschrift No. 21 03 730 describes the production of open-cell foams by the use of polyalkylene polyamines as incorporatable catalysts, organo tin catalysts could not be used on account of the shrinkage effects which they produce. (Note page 6, paragraph 2 of the Offenlegungsschrift (specification as laid open)). It would therefore be advantageous to have a process in which the cell-opener would make it possible not only to maintain the mechanical property level, but to improve mechanical properties through use of metal catalysts without reducing the level of open-cells or increasing the tendency towards shrinkage.

British Pat. No. 1,032,873 describes poly-N,N-hydroxyalkylamides of polymeric fatty acids corresponding to the following formula

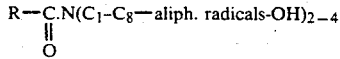

in which R is the dimerized, trimerized or polymerized residue of fatty acids containing from 8 to 24 carbon atoms. These compounds were used with polyisocyanates for the production of coatings. They were not, however, used as cell-opening additives in the production of polyurethane foams.

SUMMARY OF THE INVENTION

It is an object of the present invention to provide new poly-N,N-hydroxyalkylamides of polybasic carboxylic acids.

It is also an object of the present invention to provide new poly-N,N-hydroxyalkylamides which are particularly useful as cell-opening components for highly elastic polyurethane foams and a process for the production thereof.

It is another object of the present invention to provide a process for the production of highly elastic polyurethane foams having open-cells over their entire cross-section.

It is a further object of the present invention to provide a process for the production of highly elastic polyurethane foams having a reduced tendency to shrink which foams may be more easily recovered than prior art foams.

It is yet another object of the present invention to provide a process for the production of highly elastic polyurethane foams which are dimensionally stable during processing.

It is also an object of the present invention to provide a process for the production of highly elastic polyurethane foams having improved mechanical properties, a high level of open-cells and a reduced tendency towards shrinkage.

It is still another object of the present invention to provide a process for the production of highly elastic polyurethane foams in which metal catalysts may be successfully employed.

These and other objects which will be apparent to those skilled in the art are accomplished by reacting at a temperature of 50° to 200° C. a polycarboxylic acid alkyl or aryl ester corresponding to the formula

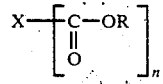

with a dialkanolamine corresponding to the formula

in which
- n represents an integer from 2 to 6;
- X represents a single bond (where $n=2$), an n-functional $C_1$-$C_{10}$-straight chain or branched alkane radical optionally substituted by a hydroxyl group, a $C_4$-$C_6$-cycloalkane radical optionally containing O, S or N-$CH_3$ in the ring, or an n-functional $C_6$-$C_{20}$-aryl radical optionally substituted by one or more hydroxyl groups;
- A represents a straight chain or branched $C_2$-$C_6$-alkylene group optionally containing an OH group; and
- R represents a $C_1$-$C_{10}$-alkyl radical or an aryl radical.

The hydroxyl compound ROH which is split off during this reaction is removed from the reaction mixture. The product recovered corresponds to the formula

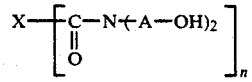

in which X, n and A are as defined above. When this poly-N,N-hydroxyalkylamide is used as a cell-opening component in the production of elastic polyurethane foams, it is generally used in an amount which 0.1 to 10 wt. % (based on mixture with compound having at least two isocyanate-reactive hydrogen atoms).

It is surprising that the use of poly-N,N-hydroxyalkylamides of polybasic aliphatic, cycloaliphatic and/or aromatic carboxylic acids in polyurethane foam formulations provided such a large number of open-cells while, at the same time, considerably reducing the tendency towards shrinkage.

It is also surprising that, use of the cell-openers of the present invention, makes it possible to foam modified (branched) aromatic diisocyanates (for example tolylene diisocyanates) containing allophanate, biuret, isocyanurate, carbodiimide, urethane and/or urea groups in the presence of organometallic urethane-forming catalysts (particularly organotin compounds, such as tin(II) carboxylates or dialkyl tin(IV) dicarboxylates) without any serious shrinkage effects being observed in the foams. Even where tin catalysts are used, a highly open-cell, shrinkage-free foam having improved mechanical properties (as reflected for example in its compression hardness) is obtained.

These improved features are also achieved by the present invention when highly branched polymeric diphenyl methane polyisocyanates are used in the production of foams.

The improvements achieved by the present invention cannot be explained by a crosslinking function of the class of compounds of the present invention, as would have been expected because serious shrinkage would result from overcrosslinking in the event of addition in high concentrations. However, the opposite result is achieved when the cell-opening material of the present invention is employed. If present in an excessive concentration, the compounds of the present invention cause the foam to collapse as a result of the intensified cell-opening effect.

DETAILED DESCRIPTION OF THE INVENTION

The present invention relates to poly-N,N-hydroxyalkylamides of polybasic, aliphatic, cycloaliphatic and/or aromatic polycarboxylic acids corresponding to the formula

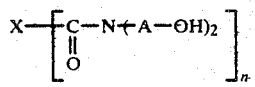

in which
  n represents an integer of from 2 to 6 (preferably from 2 to 4);
  X represents a single bond (where n=2), an n-functional, $C_1$-$C_{10}$-straight-chain or branched-chain alkane radical optionally substituted by a hydroxyl group (preferably a $C_1$-$C_4$-alkane radical), a $C_4$-$C_6$-cycloalkane radical optionally containing O, S or N—$CH_3$ as a hetero atom or group of hetero atoms in the ring, or an n-function $C_6$-$C_{20}$-aryl radical optionally substituted by one or more hydroxyl groups; and
  A represents a straight-chain or branched-chain $C_2$-$C_6$-alkylene group optionally containing an OH-group (preferably an ethylene, a 1,2- or 1,3-propane group and most preferably an ethylene group). Most preferably, X represents a single bond (n=2),
  a $C_1$-$C_6$-alkylene radical (n=2),

 radical (n = 3),

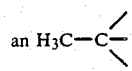 radical (n = 3),

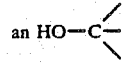 radical (n = 3),

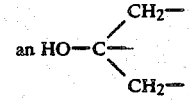 radical (n = 3),

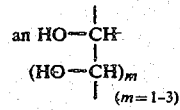 radical (n = 2)

 radical (n = 4),

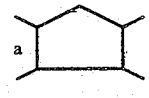 radical (n = 4), and

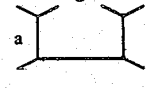 radical (n = 4),

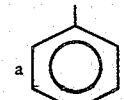 radical (n = 2),

 radical (n = 2)

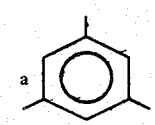 radical (n = 3),

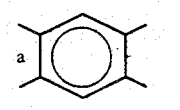 radical (n = 4)

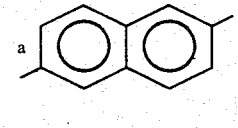 radical (n = 2),

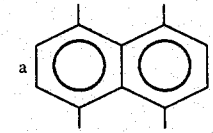 radical (n = 4),

-continued

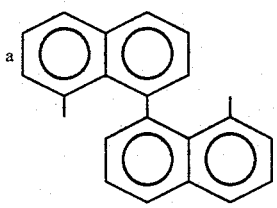 radical (n = 2),

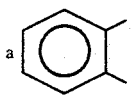 radical (n = 2),

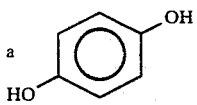 radical (n = 2), or

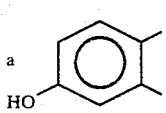 radical (n = 2).

Di-(hydroxyalkyl)-amides made from esters in which X represents a single bond,

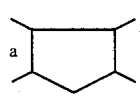 radical, a (CH$_2$)$_m$ radical in which m = 1 to 4,

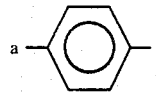 radical,

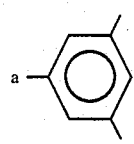 radical,

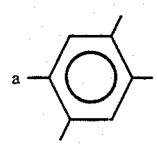 radical or

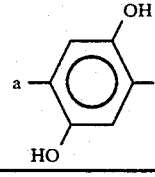 radical, are particularly preferred.

The present invention also relates to a process for producing these poly-N,N-hydroyalkylamides of polybasic polycarboxylic acids. In this process, polycarboxylic acid alkyl or aryl esters corresponding to the formula

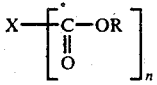

in which

X and n are as defined above and

R represents a C$_1$–C$_{10}$-(preferably C$_1$–C$_4$-) alkyl radical or an aryl radical (preferably a phenyl radical), are reacted with dialkanolamines corresponding to the formula

in which

A is as defined above, at elevated temperature (50° to 200° C. and preferably 70° to 150° C.).

The hydroxyl compound ROH split off is removed (e.g. distilled off) from the reaction mixture at atmospheric and/or reduced pressure.

The present invention also relates to the use of the compounds of the present invention for the production of open-cell polyurethane foams. Compounds containing at least 2 isocyanate-reactive hydrogen atoms and having a molecular weight of from 400 to 10,000 are reacted with polyisocyanates and, optionally, chain-extending agents having a molecular weight in the range from 18 to 400 in the presence of a catalyst, a cell-opening component, water and/or an organic blowing agent, and optionally a foam stabilizer. The poly-N,N-hydroxyalkylamides of polybasic carboxylic acids of the present invention which correspond to the formula

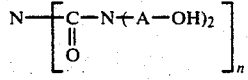

in which

X, A and n are as defined above, are used as the cell-opening component in quantities of from 0.1 to 10 wt. %, generally in quantities of from 0.5 to 7.5 wt. % and preferably in quantities of from 0.75 to 5 wt. % (based on the mixture with the compounds containing at least 2 isocyanate-reactive hydrogen atoms and having a molecular weight of from 400 to 10,000).

The cell-opening compounds of the invention are amides of polybasic carboxylic acids which are perhydroxyalkylated on the amide nitrogen. Examples of these amides are:

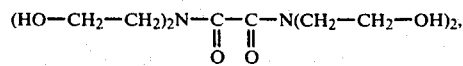

-continued
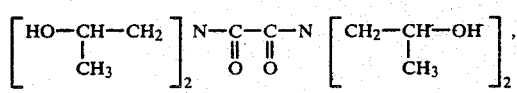
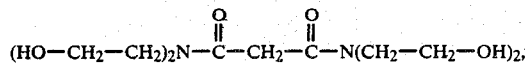
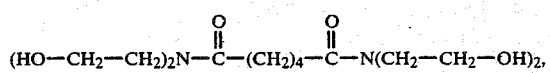
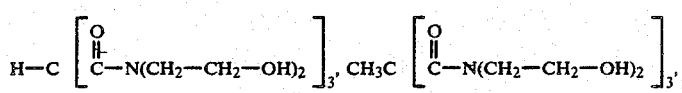
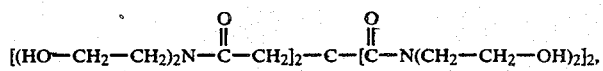
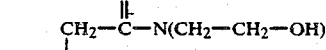
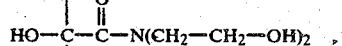
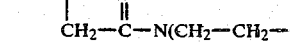
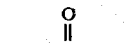
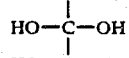
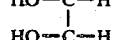
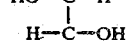
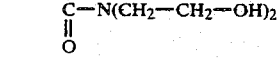
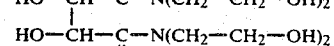
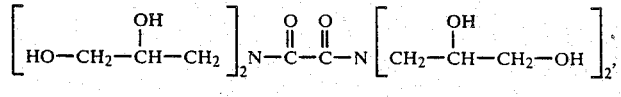
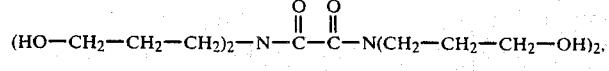

-continued
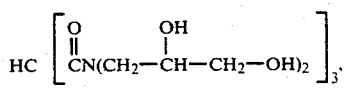
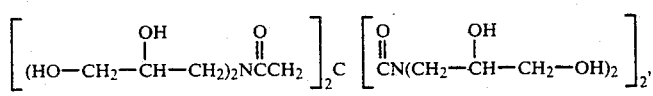
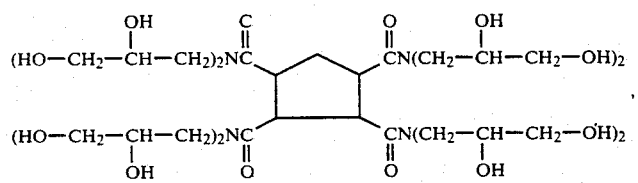
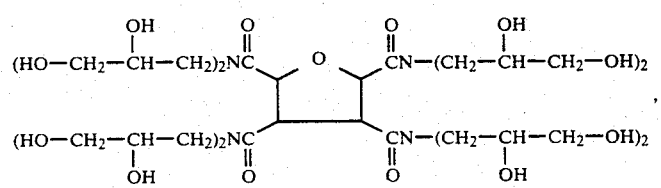
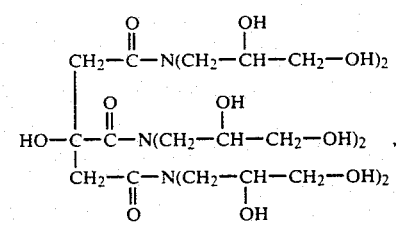
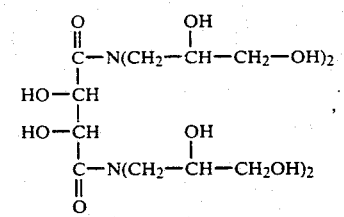
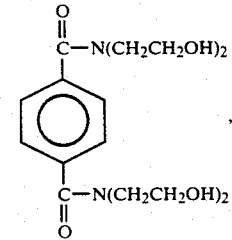
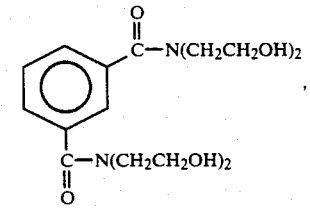
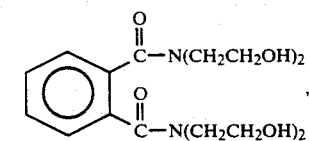

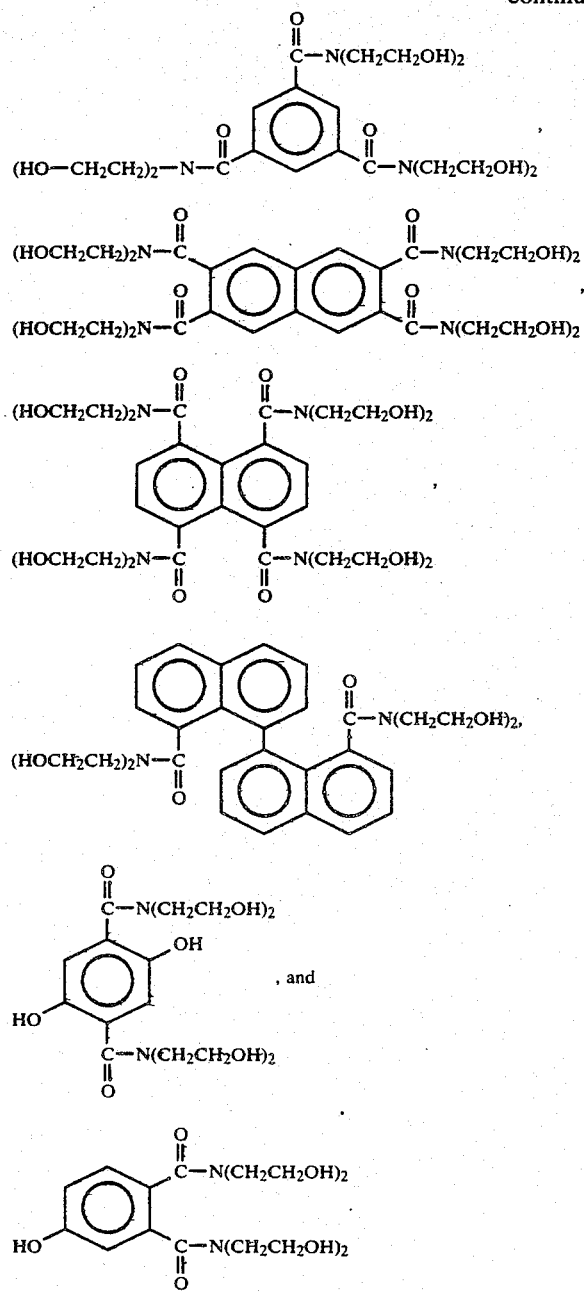

, and

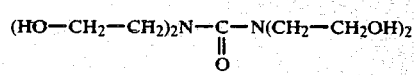

Compounds of the present invention which are particularly effective cell-openers are hydroxylalkyl derivatives of the type which contain primary hydroxy groups. Compounds in which the hydroxyalkyl groups are hydroxyethyl groups are even more effective. These hydroxyethyl amide derivatives are distinguished by their particularly intense cell-opening effect in moderate quantities (for example in quantities of from 0.5 to 2.5 wt. %).

Surprisingly, the effectiveness of the amide derivatives is largely dependent upon structure. For example, amides of carbonic acid such as $$(HO-CH_2-CH_2)_2N-\underset{\underset{O}{\|}}{C}-N(CH_2-CH_2OH)_2$$

have virtually no cell-opening effect.

The compounds of the present invention are preferably produced by aminolysis, of the corresponding alkyl or aryl esters with dialkanolamines at elevated temperature, accompanied by elimination of the alcohol component of the ester. Suitable aminolysis processes are described, for example, in Houben-Weyl, Vol. 8, pages 653 et seq. and Vol. XI/2, page 27, and in British Pat. No. 1,032,873.

Suitable foam-forming starting materials which may be used for the production of polyurethane foams using the cell-opening polyhydroxy alkylamides of polybasic carboxylic acids of the present invention are known to those in the art.

Appropriate compounds containing at least two isocyanate-reactive hydrogen atoms and having a molecular weight of generally from 400 to 10,000 are known. Such compounds may contain amino groups, thiolgroups or carboxyl groups. These isocyanate-reactive compounds may contain hydroxyl groups, (preferably from 2 to 8 hydroxyl groups) and have molecular weights preferably in the range from 800 to 6000 (most preferably in the range from 1500 to 4000). Preferred isocyanate-reactive compounds are polyesters, polyethers, polythioethers, polyacetals, polycarbonates and polyester amides containing from 2 to 4 hydroxyl groups, of the type known to be useful for the production of cellular and non-cellular polyurethanes and described, for example, in German Offenlegungsschrift No. 28 32 253, pages 11 to 18. It is particularly preferred to use polyethers of the type obtained by the addition of one or more alkylene oxides (ethylene oxide and particularly propylene oxide) with difunctional or polyfunctional "starters", propylene glycol, glycerol, sorbitol, formose, triethanolamine, trimethylol propane; and polyethers of the type containing polyaddition products of diisocyanates and hydrazine and/or diamines and/or glycols or polymers and/or graft polymers (preferably of styrene and acrylonitrile) in dispersed or dissolved form.

Compounds containing at least two isocyanate-reactive hydrogen atoms and having a molecular weight of from 18 to 399 may optionally be used as starting materials in producing polyurethane foams. Such compounds contain hydroxyl groups and/or amino groups and/or thiol groups and/or carboxyl groups and/or hydrazide groups, preferably hydroxyl groups and/or amino groups. These compounds which serve as chain-extending agents or crosslinking agents generally contain from 2 to 8 and preferably from 2 to 4 isocyanate-reactive hydrogen atoms. Examples of such compounds are described on pages 19 to 20 of German Offenlegungsschrift No. 28 32 253. Water, hydrazine, 1,4-butane diol, trimethylol propane, formitol mixtures and adipic acid dihydrazide are specific examples of appropriate chain extenders.

Aliphatic, cycloaliphatic, araliphatic, heterocyclic and, in particular, aromatic polyisocyanates of the type described for example by W. Siefken in Justus Liebigs Annalen der Chemie, 562, pages 75 to 136 are useful in making polyurethane foams in accordance with the present invention. Suitable polyisocyanates generally correspond to the formula $Q(NCO)_n$, in which $n=2$ to 4, (preferably 2) and Q is an aliphatic hydrocarbon radical containing from 2 to 18 (preferably from 6 to 12) carbon atoms, a cycloaliphatic hydrocarbon radical containing from 4 to 20 (preferably from 5 to 11) carbon atoms, an aromatic hydrocarbon radical containing from 6 to 20 (preferably from 6 to 13) carbon atoms or an araliphatic hydrocarbon radical containing from 8 to 15 (preferably from 8 to 13) carbon atoms. Specific examples of such polyisocyanates are described on pages 10 and 11 of German Offenlegungsschrift No. 28 32 253. It is preferred to use polyisocyanates which may readily be obtained on a commercial scale, such as 2,4- and/or 2,6-tolylene diisocyanate, and mixtures of these isomers ("TDI"), diphenyl methane diisocyanates (4,4'- and/or 2,4'- and/or 2,2'-isomers); polyphenyl polymethylene polyisocyanates of the type obtained by condensing aniline with formaldehyde, followed by phosgenation ("crude MDI"); and "modified polyisocyanates" containing carbodiimide groups, urethane groups, allophanate groups, isocyanurate groups, urea groups and/or biuret groups. Modified polyisocyanates of the type derived from 2,4- and/or 2,6-tolylene diisocyanate or from 4,4'- and/or 2,4'-diphenyl methane diisocyanate are most preferred.

Auxiliaries and additives which may optionally be used are readily volatile inorganic or organic compounds (as blowing agents), catalysts known to those in the art (such as tertiary amines, tin(II) and tin(IV) compounds), surface-active additives (such as emulsifiers and foam stabilizers), reaction retarders (for example acid-reacting compounds, such as hydrochloric acid, organic acid halides or organic acids), known cell regulators (such as paraffins, fatty alcohols or dimethyl polysiloxanes), pigments or dyes, known flame-proofing agents; stabilizers against the effects of ageing, light and weather, plasticizers and fungistatic and bacteriostatic compounds as well as fillers. These optional auxiliaries and additives are described in detail for example on pages 21 to 24 of German Offenlegungsschrift 27 32 292. Additional examples of suitable auxiliaries and additives may be found in Kunststoffhandbuch, Vol. VII, published by Vieweg and Hoechtlen, Carl-Hanser-Verlag, Munich 1966, pages 103 to 113.

The cell-opening polyhydroxyalkylamides of the present invention are normally mixed with the relatively high molecular weight polyol compound (for example the polyethers) in quantities such that the cell-opener is 0.1 to 10 wt. % of the mixture. This mixture may also contain the usual auxiliaries and additives. However, it is also possible to add the cell-opening compounds of the present invention together with water and other auxiliaries to the polyols or to the reaction mixture (which may even be preformed NCO-prepolymers).

The quantity in which the cell-openers of the present invention is used lies in the range of 0.1 to 10 wt. %, but the optimum amount within that range for a particular combination of reactants should be determined by a series of simple tests. A large excess of cell-opener in the mixture to be foamed results in the collapse of the foam.

Production of the foam may be carried out in accordance with techniques known to those in the art. The cell-openers of the present invention are particularly useful in the production of semi-elastic and elastic foams by block foaming or by the known laminator process. However, it is also possible to carry out foaming in a mold rather than in a free state to produce molded foam articles. When a mold is used, foaming is preferably carried out in the absence of heat (cold-hardening molded foams). In-mold foaming may be carried out in a way such that the molding has a cellular structure at its surface or such that the molding has a compact skin and a cellular core. The foamable reaction mixture may be introduced into the mold in a quantity such that the foam formed just fills the mold, or excess foamable reaction mixture may be introduced into the mold.

The foam products made in accordance with the present invention may be used for example, in furniture upholstery, mattresses, motor car seats, arm rests, sponges and structural elements as well as seat and dashboard facings.

Having thus described our invention, the following Examples are given by way of illustration. The percent- ages and parts given in these Examples are percents by weight and parts by weight, unless otherwise indicated.

EXAMPLES

EXAMPLE 1

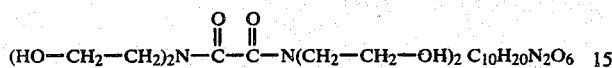
(264)

210 g (2 moles) of diethanolamine were added dropwise to 146 g (1 mole) of oxalic acid diethyl ester. The temperature rose to 90° C. and ethanol distilled off almost quantitatively. Treatment in vacuo gave 264 g (quantitative) of tetrahydroxy ethyl oxalic acid amide having a viscosity at 80° C. of 1100 cP and an OH-number of 850. The product had the following analysis:

| Calculated: | C 45.4 | H 7.57 | N 10.6 |
|---|---|---|---|
| Observed: | C 45.0 | H 7.0 | N 10.4 |

EXAMPLE 2

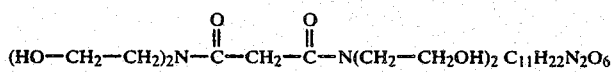
(278)

The above-shown compound was obtained by reacting 160 g (1 mole) of malonic acid diethyl ester and 210 g (2 moles) of diethanolamine in accordance with the procedure described in Example 1. 278 g (quantitative) of tetrahydroxyethyl malonic acid amide having an OH-number of 800 were produced. This product had the following analysis:

| Calculated: | C 47.5 | H 7.9 | N 9.9 |
|---|---|---|---|
| Observed: | C 47.3 | H 7.5 | N 9.7 |

EXAMPLE 3

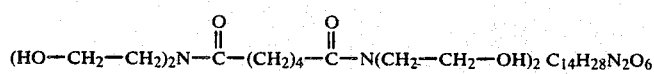
(320)

The above-shown compound was produced by reacting 174 g (1 mole) of adipic acid dimethyl ester with 210 g (2 moles) of diethanolamine in the manner described in Example 1. 320 g (quantitative) of a viscous, slowly crystallizing substance having an OH-number of 700 were recovered. This product had the following analysis:

| Calculated: | C 52.5 | H 8.75 | N 8.75 |
|---|---|---|---|
| Observed: | C 52.0 | H 8.3 | N 8.4 |

EXAMPLE 4

(404)

The above-shown compound was produced in the manner described in Example 1 from 258 g (1 mole) of decane dicarboxylic acid dimethyl ester and 210 g (2 moles) of diethanolamine. 402 g (quantitative) of a highly viscous mass were produced. This product had the following analysis:

| Calculated: | C 59.5 | H 9.88 | N 6.95 |
|---|---|---|---|
| Observed: | C 58.3 | H 9.30 | N 6.45 |

EXAMPLE 5

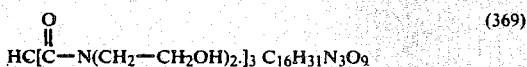
(369)

The above-shown compound was produced by the procedure described in Example 1 from 107 g (0.46 mole) of methane tricarboxylic acid triethyl ester and 145 g (1.38 mole) of diethanolamine. 189 g (quantitative) of the product having an OH-number of 910 and the following compositional analysis:

| Calculated: | C 52.0 | H 8.4 | N 11.4 |
|---|---|---|---|
| Observed: | C 51.5 | H 8.0 | N 11.2 | were recovered.

EXAMPLE 6

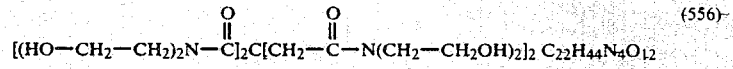
(556)

The above-shown compound was produced by the procedure described in Example 1 from 64.5 g (0.2 mole) of 3,3-bis-ethoxycarbonyl glutaric acid diethyl ester and 84 g (0.8 mole) of diethanolamine. 106 g (quantitative) of a highly viscous residue having an OH-number of 800 were produced. The product had the following compositional analysis:

| Calculated: | C 47.7 | H 7.9 | N 10.0 |
|---|---|---|---|
| Observed: | C 47.0 | H 7.4 | N 9.7 |

EXAMPLE 7

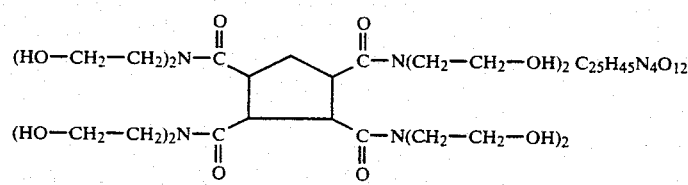
(593)

The above-shown compound was produced by the procedure described in Example 1 from 75.5 g (0.25 mole) of 1,2,3,4-cyclopentane tetracarboxylic acid methyl ester and 105 g (1 mole) of diethanolamine. 146 g (quantitative) of octahydroxyethyl-1,2,3,4-cyclopentane tetracarboxylic acid amide having an OH-number of 750 were recovered. The product had the following compositional analysis:

| Calculated: | C 50.6 | H 7.6 | N 9.4 |
|---|---|---|---|
| Observed: | C 50.0 | H 7.1 | N 9.3 |

EXAMPLE 8

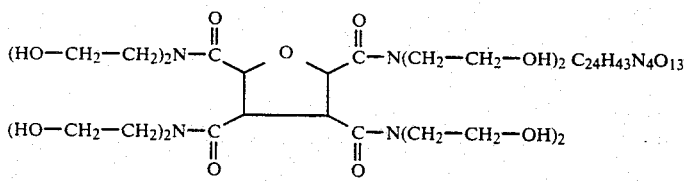
(595)

The above-shown compound was obtained by the procedure described in Example 1 from 76 g (0.25 mole) of tetrahydrofuran-2,3,4,5-tetracarboxylic acid methyl ester and 105 g (1 mole) of diethanolamine. 149 g (quantitative) of octahydroxyethyl-tetrahydrofuran-2,3,4,5-tetracarboxylic acid amide having an OH-number of 750 were obtained. The product had the following compositional analysis:

| Calculated: | C 48.4 | H 7.2 | N 9.4 |
|---|---|---|---|
| Observed: | C 48.2 | H 7.0 | N 9.2 |

EXAMPLE 9

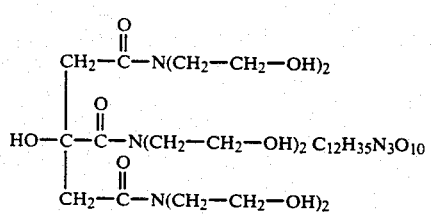
(453)

The above-shown compound was obtained by the procedure described in Example 1 from 117 g (0.5 mole) of citric acid trimethyl ester and 157.5 g (1.5 mole) of diethanolamine. 220 g (quantitative) of hexahydroxyethyl citric acid amide having an OH-number of 860 were obtained. This product had the following elemental analysis:

| Calculated: | C 47.6 | H 7.7 | N 9.3 |
|---|---|---|---|
| Observed: | C 47.1 | H 7.2 | N 9.1 |

EXAMPLE 10

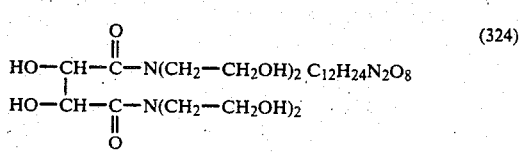
(324)

The above-shown compound was obtained by the procedure described in Example 1 from 89 g (0.5 mole) of tartaric acid dimethyl ester and 105 g (1 mole) of diethanolamine. 160 g (quantitative) of tetrahydroxyethyl tartaric acid amide having an OH-number of 1040 were obtained. The product had the following elemental analysis:

| Calculated: | C 44.4 | H 7.5 | N 8.6 |
|---|---|---|---|
| Observed: | C 44.0 | H 7.2 | N 8.3 |

EXAMPLE 11

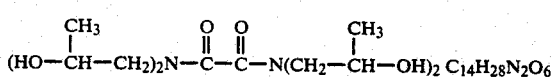
(320)

The above-shown compound was produced by the procedure described in Example 1 from 266 g (2 moles) of diisopropanolamine and 146 g (1 mole) of oxalic acid diethyl ester. 320 g (quantitative) of tetra-(2-hydroxypropyl)-oxalic acid amide having the following elemental analysis:

| Calculated: | C 52.5 | H 8.75 | N 8.75 |
|---|---|---|---|
| Observed: | C 51.0 | H 8.4 | N 8.3 | were obtained.

EXAMPLE 12

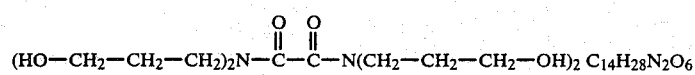
(320)

The above-shown compound was produced by the procedure described in Example 1 from 133 g (1 mole) of bis-(3-hydroxypropyl)-amine and 73 g (0.5 mole) of oxalic acid diethyl ester. 160 g (quantitative) of tetra-(3-hydroxypropyl)-oxalic acid amide having the following elemental analysis:

| Calculated: | C 52.5 | H 8.75 | N 8.75 |
|---|---|---|---|
| Observed: | C 51.3 | H 8.3 | N 8.6 | were obtained.

EXAMPLE 13

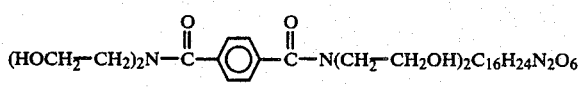
(340)

Methanol was slowly distilled off from 210 g (2 moles) of diethanolamine and 194 g (1 mole) of terephthalic acid dimethyl ester. A clear solution was formed. This solution was then treated in a high vacuum at 120° to 140° C. A highly viscous reaction product which crystallized after prolonged standing was formed in a quantitative amount. This product dissolved smoothly in water, had an OH-number of 656 and the following elemental analysis:

| Calculated: | C 56.5 | H 7.06 | N 8.24 |
|---|---|---|---|
| Observed: | C 55.9 | H 6.90 | N 8.10 |

EXAMPLE 14

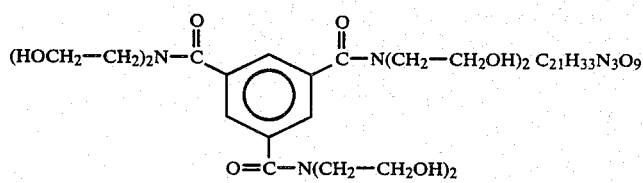
(471)

Methanol was slowly distilled off from 252 g (1 mole) of trimesic acid trimethyl ester and 315 g (3 moles) of diethanolamine. A clear, viscous solution was formed. A high vacuum was then applied at 120° to 140° C. The reaction product which solidified in glass-like form was obtained in a quantitative yield. The product which was smoothly soluble in water had the following elemental analysis:

| Calculated: | C 53.5 | H 7.0 | N 8.9 |
|---|---|---|---|

-continued

| Observed: | C 52.8 | H 6.8 | N 8.7 |
|---|---|---|---|

EXAMPLE 15

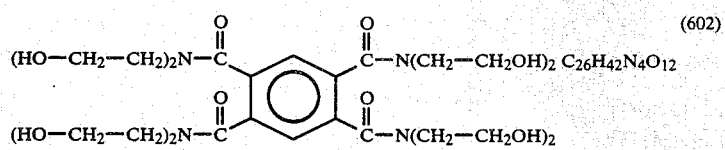
(602)

Methanol was distilled off from 310 g (1 mole) of pyromellitic acid tetramethyl ester and 420 g (4 moles) of diethanolamine. A clear, viscous solution formed. Residual solvent was distilled off in a high vacuum at 130° to 140° C. until a highly viscous reaction product solidifying in glass-like form was obtained. This product dissolved smoothly in water, had an OH-number of 745 and the following elemental analysis:

| Calculated: | C 51.7 | H 6.97 | N 9.3 |
|---|---|---|---|
| Observed: | C 50.3 | H 6.80 | N 9.2 |

EXAMPLE 16

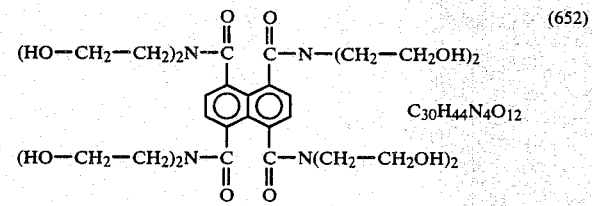
(652)

Methanol was distilled off from 360 g (1 mole) of 1,4,5,8-naphthalene tetracarboxylic acid tetramethyl ester and 420 g (4 moles) of diethanolamine. A clear, viscous solution gradually formed. Volatile substances were distilled off from this solution in a high vacuum at 140° C. A highly viscous reaction product which solidified in glass-like form was obtained in a quantitative yield. This product dissolved smoothly in water, had an OH-number of 685, and had the following elemental analysis:

| Calculated: | C 55.2 | H 6.75 | N 8.6 |
|---|---|---|---|
| Observed: | C 54.3 | H 6.55 | N 8.4 |

EXAMPLE 17

A mixture of
- 100 parts by weight of a trimethylol-propane-started-poly-(oxyethylene-oxypropylene)-triol having an average molecular weight of 6000 and an OH-number of 28;
- 3.0 parts by weight of water;
- 0.2 parts by weight of triethylene diamine;
- 3.6 parts by weight of diisopropanolamine;
- 1.5 parts by weight of triethanolamine;
- 2.0 parts by weight of trichloroethylphosphate;
- 0.3 parts by weight of a chlorine-containing polysiloxane stabilizer;
- 0.1 part by weight of tin dioctoate; and
- 1.2 parts by weight of tetra-(hydroxyethyl)-oxalic acid amide as the cell-opener according to the invention (prepared in Example 1)

was reacted with 58.3 parts by weight of an allophanatized tolylene diisocyanate having an NCO-content of 40.5 % in a continuous block foaming reactor of the UBT type as produced by Maschinenfabrik Hennecke/Birlinghoven (Federal Republic of Germany). An open-cell, non-shrinking highly elastic foam was formed.

COMPARISON EXAMPLE 17a

For comparison, the foam described in Example 17 was produced without the addition of tetrahydroxyethyl oxalic acid amide. The resulting foam had closed cells and underwent considerable shrinkage on cooling.

COMPARISON EXAMPLE 17b

For further comparison, the foam described in Example 17 was produced without the addition of tetrahydroxyethyl oxalic acid amide and without the addition of tin dioctoate. The highly elastic foam thus produced showed only slight surface shrinkage phenomena. However, its tensile and breaking elongation properties were considerably poorer than in Example 17.

The mechanical properties of the foams produced in accordance with Example 17 and Comparison Example 17b are compared in Table 1 below:

TABLE 1

| | Example 17 | Comparison Example 17b |
|---|---|---|
| Gross density kg/m$^3$ | 35 | 34 |
| Tensile strength kPa | 115 | 90 |
| Breaking elongation % | 140 | 110 |
| Compression hardness kPa at 40% compression | 2.4 | 2.4 |

COMPARISON EXAMPLE 17c 11 parts by weight of tetrahydroxyethyl oxalic acid amide were incorporated in the mixture of Example 17. The foamable mixture collapsed during the rise phase.

EXAMPLE 18

A mixture of
- 100 parts by weight of a trimethylol-propane-started poly-(oxyethylene-oxypropylene)-triol having an OH-number of 35;
- 2.6 parts by weight of water;
- 0.133 part by weight of triethylene diamine;
- 0.2 part by weight of dimethylaminoethyl ether;
- 0.2 part by weight of a chlorine-containing polysiloxane stabilizer; and
- 2.0 parts by weight of an 80% solution of octahydroxy ethyl-1,2,3,4-cyclopentane tetracarboxylic acid amide in water (prepared in Example 7)

was reacted with 53.5 parts by weight of a diphenyl methane diisocyanate mixture (binuclear component content: 85%, NCO-content: 32.5%) in a continuous block foaming reactor of the UBT type. An open-cell, non-shrinking elastic foam having the following mechanical properties was formed:
- Gross density kg/m$^3$: 35
- Tensile strength kPa: 105
- Breaking elongation %: 130
- Compression hardness kPa at 40% compression: 2.7

COMPARISON EXAMPLE 18a

For comparison, a foam was produced in the same way as in Example 18, but without the addition of octahydroxy ethyl-1,2,3,4-cyclopentane tetracarboxylic acid amide. After cooling the foam had undergone complete shrinkage.

EXAMPLE 19

A mixture of
- 66 parts by weight of a trimethylol-propane-started polyol-(oxyethylene-oxypropylene)-triol having an OH-number of 35;
- 33 parts by weight of a trimethylol-propane-started poly-(oxyethylene-oxypropylene)-triol containing 25% of a polymeric filler of acrylonitrile/styrene and having an OH-number of 26;
- 3.0 parts by weight of water;
- 0.15 parts by weight of a 33% solution of triethylene diamine in dipropylene glycol;
- 0.1 part by weight of dimethylaminoethylether;
- 1.5 parts by weight of diethanolamine;
- 0.5 part by weight of a chlorine-containing polysiloxane stabilizer;
- 0.1 part by weight of tin dioctoate; and
- 1.0 part by weight of tetrahydroxyethyl malonic acid amide (prepared in Example 2)

was reacted in an open vessel with 38.7 parts by weight of tolylene diisocyanate (80/20). An open-cell, non-shrinking highly elastic foam having the following mechanical properties was formed:
- Gross density kg/m$^3$: 32
- Tensile strength kPa: 110
- Breaking elongation %: 164
- Compression hardness at 40% compression: 2.5

A comparison foam made without the tetrahydroxyethyl malonic acid amide contained a large number of closed cells and had to be mechanically opened up before cooling.

EXAMPLE 20

A mixture of
- 100 parts by weight of a trimethylol-propane-started poly-(oxyethylene-oxypropylene)-triol having an average molecular weight of 6000 and an OH-number of 28;
- 3.0 parts by weight of water;
- 0.2 part by weight of triethylene diamine;
- 3.6 parts by weight of diisopropanolamine;
- 1.5 parts by weight of triethanolamine;
- 2.0 parts by weight of trichloroethyl phosphate;
- 0.3 parts by weight of a chlorine-containing polysiloxane stabilizer;

0.1 part by weight of tin dioctoate; and
1.2 parts by weight of tetra-(3-hydroxypropyl)-oxalic acid amide as the cell-opener according to the invention (prepared in Example 12)

was reacted with 58.3 parts by weight of an allophanatized tolylene diisocyanate having an NCO-content of 40.5% in a continuous block foaming reactor of the UBT type. An open-cell, non-shrinking highly elastic foam was formed.

EXAMPLE 21

A mixture of
100 parts by weight of a trimethylol-propane-started poly-(oxyethylene-oxypropylene)-triol having an average molecular weight of 6000 and an OH-number of 28;
3.0 parts by weight of water;
0.2 part by weight of triethylene diamine;
3.6 parts by weight of diisopropanolamine;
1.5 parts by weight of triethanolamine;
2.0 parts by weight of trichloroethyl phosphate;
0.3 part by weight of a chlorine-containing polysiloxane stabilizer;
0.1 part by weight of tin dioctoate; and
1.5 parts by weight of an 80% solution of tetra-hydroxyethyl)-terephthalic acid amide in water (prepared in Example 13) as the cell-opener according to the invention was intensively mixed with 58.3 parts by weight of an allophanatized tolylene diisocyanate having an NCO-content of 40.5%. The resulting mixture was foamed in an open mold. An open-cell, non-shrinking highly elastic foam was formed.

EXAMPLE 22

A mixture of
100 parts by weight of a trimethylol-propane-started poly-(oxyethylene-oxypropylene)-triol having an average molecular weight of 6000 and an OH-number of 28;
3.0 parts by weight of water;
0.2 part by weight of triethylene diamine;
3.6 parts by weight of diisopropanolamine;
1.5 parts by weight of triethanolamine;
2.0 parts by weight of trichloroethyl phosphate;
0.3 part by weight of a chlorine-containing polysiloxane stabilizer;
0.1 part by weight of tin dioctoate; and
1.5 parts by weight of an 80% solution of hexa(hydroxyethyl)-trimesic acid amide in water (prepared in Example 14) as the cell-opener according to the invention was intensively mixed with 58.3 parts by weight of an allophanatized tolylene diisocyanate having an NCO-content of 40.5%. The resulting mixture was foamed in an open mold. An open-cell, non-shrinking highly elastic foam was formed.

EXAMPLE 23

A mixture of
100 parts by weight of the polyether of Example 21;
3.0 parts by weight of water;
0.2 part by weight of triethylene diamine;
3.6 parts by weight of diisopropanolamine;
1.5 parts by weight of triethanolamine;
2.0 parts by weight of trichloroethyl phosphate;
0.3 part by weight of a chlorine-containing polysiloxane stabilizer;
0.1 part by weight of tin dioctoate; and
1.5 parts by weight of an 80% solution of octa(hydroxyethyl)-pyromellitic acid amide in water (prepared in Example 15) as the cell-opener according to the invention was intensively mixed with 58.3 parts by weight of an allophanatized tolylene diisocyanate having an NCO-content of 40.5%. The resulting mixture was foamed in an open mold. An open-cell, non-shrinking highly elastic foam was formed.

What is claimed is:

1. A process for the production of an open-cell polyurethane foam in which a compound having at least two isocyanate-reactive hydrogen atoms and a molecular weight of from 400 to 10,000 and a polyisocyanate are reacted in the presence of a catalyst, a blowing agent and 0.1 to 10 wt. % cell-opening component (based on mixture with compound having at least two isocyanate-reactive hydrogen atoms) said cell-opening component corresponding to the formula

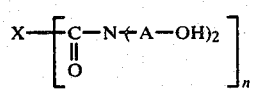

in which
n represents an integer from 2 to 6;
X represents a single bond (where n=2), an n-functional $C_1$–$C_{10}$-straight chain or branched alkane radical optionally substituted by a hydroxyl group, a $C_4$–$C_6$-cycloalkane radical optionally containing O, S or N—$CH_3$ in the ring, or an n-functional $C_6$–$C_{20}$ aryl radical optionally substituted by one or more hydroxyl groups; and
A represents a straight chain or branched $C_2$–$C_6$-akylene group optionally containing an OH group.

2. The process of claim 1 wherein a chain-extending agent having a molecular weight from 18 to 400 is included in the reaction mixture.

3. The process of claim 1 wherein a foam stabilizer is included in the reaction mixture.

4. A process for the production of an open-cell polyurethane foam in which a compound containing at least two isocyanate-reactive hydrogen atoms and having a molecular weight of from 400 to 10,000 is reacted with a modified, branched aromatic diisocyanate containing allophanate, biuret, isocyanurate, carbodiimide, urethane and/or urea groups in the presence of an organometallic catalyst, a blowing agent and 0.5 to 7.5 wt. % (based on mixture with compound containing isocyanate-reactive hydrogen atoms) of a cell-opening component said cell-opening component corresponding to the formula

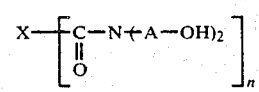

in which
n represents an integer from 2 to 6;
X represents a single bond (where n=2), an n-functional $C_1$–$C_{10}$-straight chain or branched alkane radical optionally substituted by a hydroxyl group, a $C_4$–$C_6$-cycloalkane radical optionally containing O, S or N—$CH_3$ in the ring, or an n-functional $C_6$-$C_{20}$ aryl radical optionally substituted by one or more hydroxyl groups; and A represents a straight chain or branched $C_2$-$C_6$-alkylene group optionally containing an OH group.

5. The process of claim 4 wherein A represents —$CH_2$—$CH_2$— and/or —$CH_2$—$CH_2$—$CH_2$—.

6. The process of claim 4 wherein a chain-extending agent having a molecular weight from 18 to 400 is included in the reaction mixture.

7. The process of claim 4 wherein foam stabilizer is included in the reaction mixture.

8. The process of claim 4 wherein the modified, bran aromatic diisocyanate is tolylene diisocyanate.

9. The process of claim 8 wherein the cell-opening component is used in a quantity from 0.5 to 2.5 wt. % (based on mixture with compound containing at least two isocyanate-reactive hydrogen atoms).

10. The process of claim 9 wherein the radical A of cell-opening component is the $CH_2$—$CH_2$ group.

11. The process of claim 10 wherein the catalyst is a tin(II) carboxylate or a dialkyl tin(IV) dicarboxylate.

12. The process of claim 11 wherein a foam stabilizer is included in the reaction mixture.

13. The process of claim 4 in which the blowing agent is water.

14. The process of claim 4 in which the cell-opening component is N,N,N',N'-tetrakis-(2-hydroxyethyl)-malonic acid diamide.

15. The process of claim 1 in which the blowing agent is water.

16. The process of claim 1 in which the cell-opening component is N,N,N',N'-tetrakis-(2-hydroxyethyl)-malonic acid diamide.

* * * * *